United States Patent [19]

Herscovici et al.

[11] Patent Number: 4,470,418
[45] Date of Patent: Sep. 11, 1984

[54] DUAL CHANNEL CARDIAC PACER ISOLATION CIRCUIT

[75] Inventors: Hari Herscovici, Miami Beach; Peter P. Tarjan, Miami, both of Fla.

[73] Assignee: Cordis Corporation, Miami, Fla.

[21] Appl. No.: 375,198

[22] Filed: May 5, 1982

[51] Int. Cl.³ .............................................. A61N 1/36
[52] U.S. Cl. ............................................ 128/419 PG
[58] Field of Search .............. 128/419 PG, 731, 696, 128/902, 908, 419 P

[56] References Cited

U.S. PATENT DOCUMENTS

| | | | |
|---|---|---|---|
| 3,135,264 | 6/1964 | Tischler et al. | 128/423 |
| 3,669,120 | 1/1972 | Nielsen | 128/419 PG |
| 3,903,897 | 9/1975 | Woollons et al. | 128/419 PG |
| 3,920,024 | 11/1975 | Bowers | 128/419 PG |
| 3,985,142 | 10/1976 | Wickham | 128/419 PG |
| 4,248,238 | 2/1981 | Joseph | 128/419 PG |
| 4,300,566 | 11/1981 | Stindt et al. | 128/419 PG |

Primary Examiner—William E. Kamm
Assistant Examiner—Mitchell J. Shein
Attorney, Agent, or Firm—Kenway & Jenney

[57] ABSTRACT

Interchannel crosstalk in an existing dual channel pacer designed for bipolar leads is reduced by inserting a switching circuit between the pacing leads and the pacer terminals. In one embodiment, in each channel an isolation resistance and buffer amplifier in series with the lead electrodes, respectively, are shunted during stimulation. In another embodiment, the lead electrodes are connected to a pair of differential amplifiers which are bypassed during stimulation on a given channel.

11 Claims, 7 Drawing Figures

DUAL CHANNEL CARDIAC PACER ISOLATION CIRCUIT

CROSS-REFERENCE TO RELATED APPLICATION

The subject matter of this application is related to that of U.S. patent application Ser. No. 375,040 (Cordis 97A&C), entitled "Dual Channel Cardiac Pacer Isolation Circuit", filed simultaneously herewith, by the same inventors, assigned to the assignee of the present application and incorporated by reference herein.

BACKGROUND OF THE INVENTION

The invention relates generally to cardiac pacers, and more particularly to means for preventing crosstalk between bipolar pacer leads.

There are two major pumping chambers in the heart, the left and right ventricles. Simultaneously contracting, these chambers expel blood into the aorta and the pulmonary artery. Blood enters the ventricles from the left and right atria, respectively. The contractions arise from a wave of electrical excitation which begins in the right atrium and spreads to the left atrium. The excitation enters the atrio-ventricular (AV) node which delays its passage via the bundle of His into the ventricles. The atria contract in a separate action which precedes the major ventricular contraction by an interval of about 100 milliseconds (ms), known as the AV delay. Atrial contractions begin every 400–1,000 ms at a steady metabolically determined frequency known as the "sinus" rate, which increases with exercise, the AV delay being foreshortened at higher rates.

Electrical signals corresponding to the contractions appear in the electrocardiogram. A signal known as the P-wave accompanies atrial contraction while a signal known as the QRS complex, with a predominant R-wave, accompanies the ventricular contraction. The P and R-waves can be reliably detected as timing signals by electrical leads in contact with the respective heart chambers.

The typical implanted cardiac pacer operates by producing stimulation pulses to supply missing excitation via an insulated wire (or "pacing lead") terminating distally in an electrode attached to the right ventricle. The R-wave can be sensed by the same lead to inhibit or trigger stimulation or to restart a timing interval as in "demand" pacing. An additional lead contacts the atrium to sense P-waves, if desired. Pacers whose ventricular stimulation is timed from the sensing of a P-wave are referred to as AV synchronous or "physiological" pacers since they preserve the natural sinus rate as well as the normal sequence of contractions. In AV sequential pacers, sometimes the atrial lead is also used for atrial stimulation. Examples of physiological AV sequential pacers or "double demand" pacers in which the atrial and ventricular leads can both stimulate and sense are shown in pending U.S. Patent Application Ser. No. 153,422 entitled "Ventricular Inhibited Cardiac Pacer" filed May 27, 1980 and U.S. Patent Application Ser. No. 207,003 entitled "Multi-Mode Microprocessor Based Programmable Cardiac Pacer" filed Nov. 14, 1980, both assigned to the assignee of the present application, and incorporated herein by reference in their entirety.

There are two basic types of electrode systems used in pacing leads. Unipolar leads terminate distally in a single electrode (cathode) and employ the case of the pulse generator itself, or a conductive plate on the case, as the return electrode or ground (anode). Bipolar pacing leads, on the other hand, terminate distally in two spaced insulated electrodes connected to the pulse generator through respective wires in the pacing lead. Thus, each bipolar lead carries a positive and negative electrode for the respective chamber, and the case is not designed to form a part of the electrical circuit in this configuration.

In an AV sequential bipolar lead pacing system, bipolar pacing leads extend into the right atrium and right ventricle. In a pacer having a common ground connection, the two positive electrodes on the respective bipolar leads are tied together electrically. This shared ground connection can present crosstalk problems in both sensing and stimulation when each bipolar lead is in a different heart chamber. This is an extremely important problem to solve for physiological pacers which provide bipolar stimulation and sensing for both heart chambers with the same implanted pacer powered by a single battery.

One of the ways previously used to accomplish some measure of isolation between bipolar leads is to employ a transformer to couple the output stage of the pacing circuit to one of the leads to isolate the bipolar lead electrodes from each other. This approach, however, has only been practical when sensing is done only on one channel. In addition, it has the serious drawback of adding a relatively bulky inefficient component to the otherwise miniaturized pacer electronics.

SUMMARY OF THE INVENTION

Accordingly, the general purpose of the invention is to reduce interchannel crosstalk effectively and reliably with a minimum of additional circuitry. Interchannel crosstalk in an existing dual channel pacer designed for bipolar leads is reduced by inserting a switching circuit between the pacing leads and the pacer terminals. In one embodiment, in each channel an isolation resistance and buffer amplifier are connected in series, respectively, with the anode and cathode of each of the leads. These extra series components are shunted on the channel undergoing stimulation. In another embodiment, the lead electrodes are connected to a pair of differential amplifiers which are bypassed during stimulation on a given channel. A pair of monostable or "one-shot" circuits are triggered by the respective stimulation outputs of the existing pacer. The one-shot outputs connect the pacer leads directly for stimulation, and, in the differential amplifier embodiment, remove the power supply for the corresponding differential amplifier. A double ended power supply is created for the differential amplifiers and anti-cross-sensing logic is employed to block the atrial channel whenever an R-wave is detected. To avoid duplication, the sense amplifiers in the existing pacer may be obviated by providing the differential amplifiers with sufficient gain and threshold-detecting their outputs to provide digital sense signals.

DESCRIPTION OF THE PREFERRED EMBODIMENT

Figure 1:
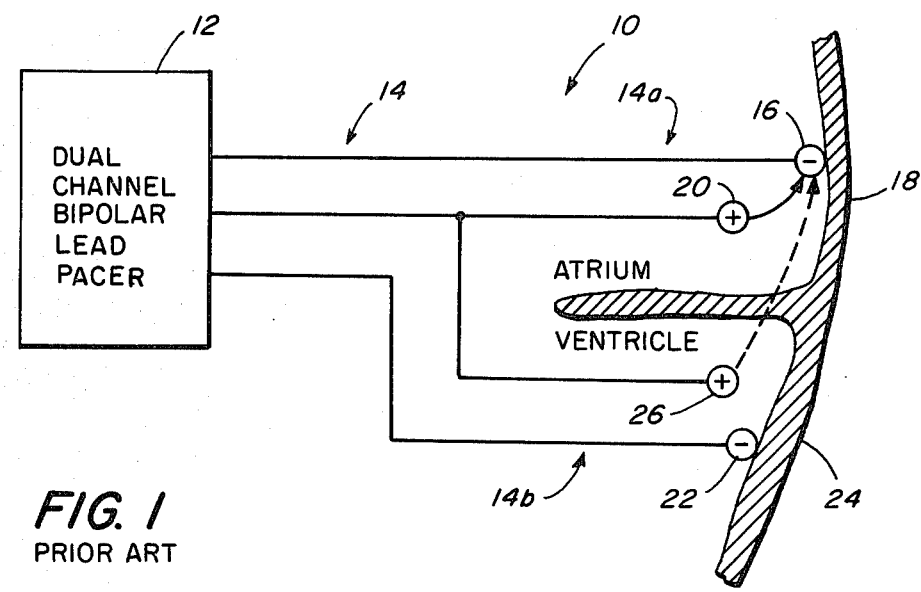
FIG. 1 is a schematic representation of a prior art dual channel bipolar lead pacer system.

FIG. 1 shows an AV sequential bipolar lead pacing system 10 including a double demand cardiac pacer pulse generator 12 containing the pacing logic circuitry sealed together with the battery cells in the customary biologically compatible hermetic enclosure. The pacer pulse generator 12 itself is implanted at a suitable location in the body, such the axillary region, and is electrically interconnected with a three conductor pervenous pacer lead 14 which terminates in an atrial lead 14a having a negative electrode 16 in contact with the inside of the right atrium 18 and a positive electrode or anode 20 spaced from the cathode. The ventricular portion 14b of the pacer lead terminates in a negative electrode 22 in contact with the ventricular wall 24 and a spaced anode 26. The anodes 20 and 26 share a common electrical connection and are thus at the same reference potential. In sensing, a "spurious" electrical potential can be established by the heart itself between the ventricular anode 26 and the atrial cathode 16 resulting in a signal to the pacer which appears to have originated in the atrium alone. The electrical path between atrial electrode 16 and 20 offers less resistance, of course, and is therefore the expected site of stimulation when the pacer pulse generator 12 applies an electrical potential between these electrodes. However, the ventricular anode 26 may inadvertently become part of the electrical circuit and cause undesirable cross stimulation. The same type of crosstalk on sensing or stimulation can occur on the ventricular channel through cathode 22 in relation to anodes 20 and 26.

Figure 2:
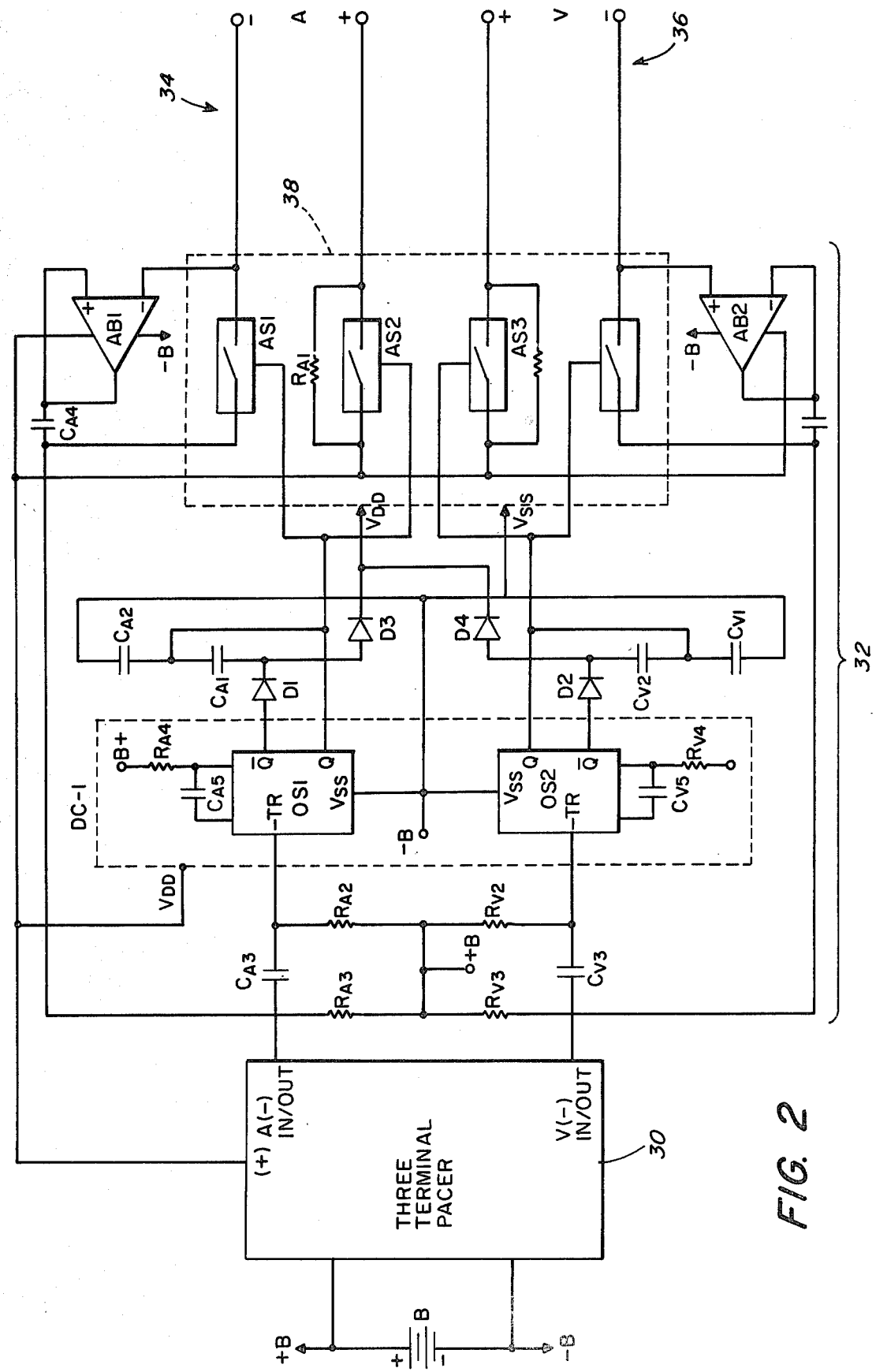
FIG. 2 is a schematic and block diagram of an interchannel isolation system according to the invention.

The circuit of FIG. 2 provides a solution to this problem in the context of an existing three terminal implantable cardiac pacer 30. The battery B which powers the pacer has its positive terminal (reference potential) connected to a positive output terminal designed to be coupled to both of the anodes on two bipolar leads, as in FIG. 1. Separate atrial and ventricular input/output terminals on the pacer are provided for connection to the cathodes of the respective leads. Without interfering with the circuitry inside pacer 30, switching circuit 32 is inserted between the bipolar leads 34 and 36 and the pacer pulse generator 30. In this embodiment the pervenous pacing lead carries four conductors, one for each distal electrode. Resistors $R_{A1}$ and $R_{V1}$ are placed in series with the lead anodes, respectively. The cathode of each lead is connected to the respective pacer terminal via buffer amplifiers AB1 and AB2 and capacitors $C_{A4}$ and $C_{V4}$, respectively. In the sensing mode, the resistances $R_{A1}$ and $R_{V1}$ isolate the two channels. The buffer amplifiers compensate for the presence of the resistors. During stimulation on a given channel, all of the extra series components on a given channel are shunted out by compound analog switch circuit 38. Thus, in the atrial channel, analog switch AS1 of circuit 38 shunts buffer amplifier AB1 and capacitor $C_{A4}$ while analog switch AS2 shunts resistor $R_{A1}$. Switches AS1 and AS2 are closed simultaneously by the output of a corresponding one of a pair of one-shot circuits DC-1 each having an astable period of approximately 59 ms. The corresponding one-shot (OS1) is triggered by the stimulation ouput via decoupling capacitor $C_{A3}$ from the atrial terminal of the pacer. Both sides of the output capacitors $C_{A3}$ and $C_{V3}$ are connected to positive reference potential B+ via respective resistors, as shown, to adjust the triggering pulses for the one-shots to a level below the power supply voltage (4.2 v battery) where voltage doublers inside the pacer 30 are used to produce an 8 v output pulse. Likewise, the analog switches should also be supplied at 8 v. Thus on the atrial side the diode and capacitive network $D_1$, $C_{A1}$ and $C_{A2}$ is employed as a voltage doubler to supply the corresponding analog switches. The ventricular channel has a similar arrangement with a one-shot and voltage doubler network which separately operates and supplies the ventricular analog switches. The doubler voltage supplies are not shown in the following embodiments, but it is intended that they be used there too, if necessary.

Figure 3:
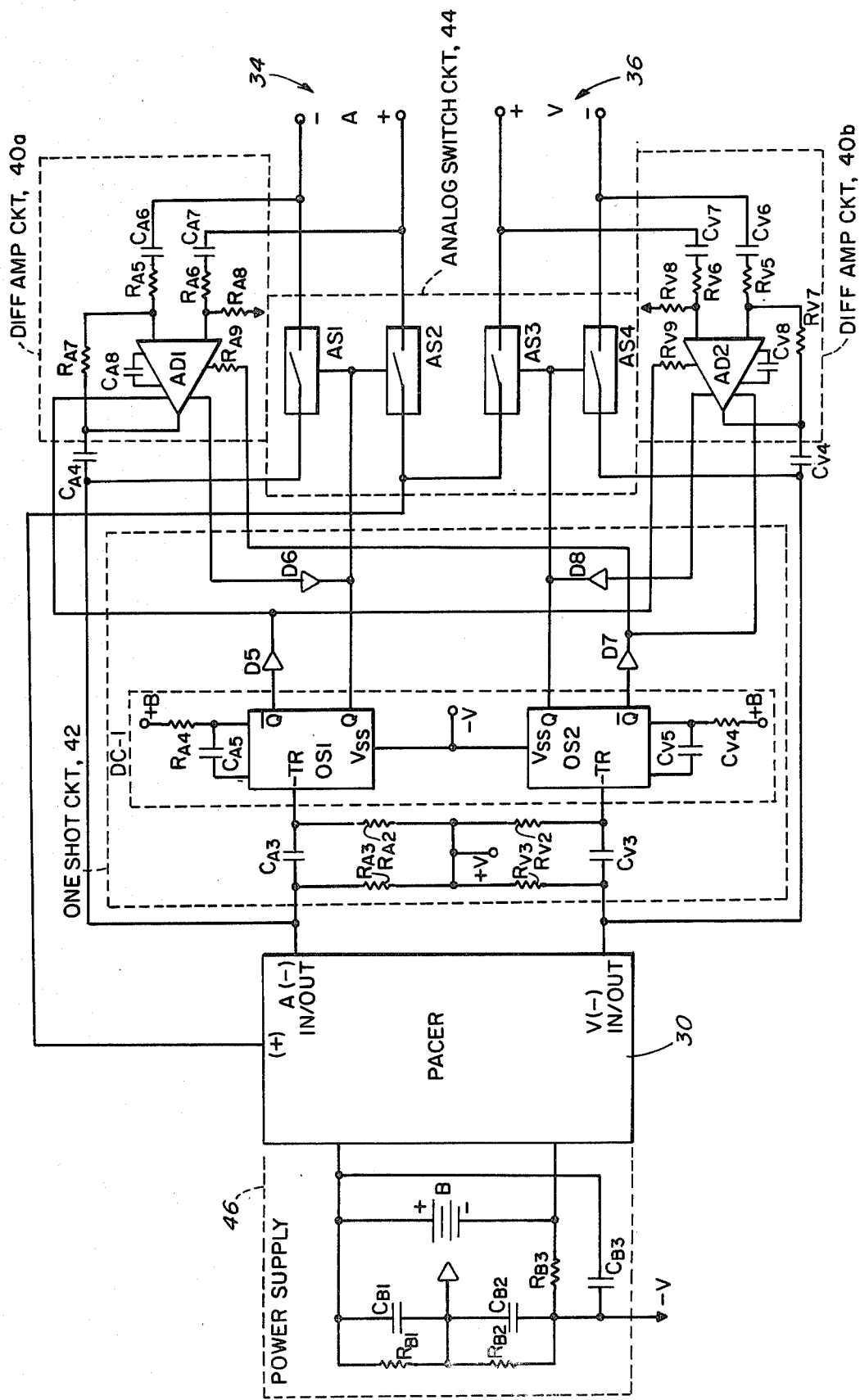
FIG. 3 is a block and schematic diagram of another embodiment of the interchannel isolation system according to the invention.

The buffer amplifiers AB1 and AB2 of FIG. 1 as well as the interchannel isolation resistors $R_{A1}$ and $R_{V1}$, are replaced in the circuit of FIG. 3 by two unitary gain differential amplifier circuits 40a and 40b to increase noise rejection. Complementary diodes D5, D6 and D7, D8 in one-shot circuit 42 supply the corresponding differential amplifiers AD1 and AD2 in the absence of stimulation on the respective channel. The Q outputs of the one-shots OS1 and OS2 control the atrial switches AS1 and AS2 and ventricular switches AS3 and AS4 of analog switch circuit 44, respectively, as in the circuit of FIG. 2.

Power supply circuit 46 (FIG. 3) establishes a midpoint ground between +B and −B required for operation of the differential amplifier circuits 40a and 40b. An output pulse tends to cause a momentary dip in battery voltage which might affect the differential amplifier outputs. Circuit 46 includes a resistive-capacitive filter formed by $R_{B3}$ and $C_{B3}$ to alleviate this effect. This filter can be used as necessary on any of the differential amplifier embodiments described herein.

The circuits described above provide the necessary isolation so that the signals issued by the heart itself will be processed, as they are, without distortion. However, in many cases it happens that the R-wave developed in the ventricle actually produces a signal in the atrium too. This signal follows the P-wave signal originating in the atrium after the corresponding AV delay and has an amplitude generally lower than the P-wave. Yet, there are cases in which the amplitude of this cross-signal is larger, equal or slightly smaller than the P-wave and with almost the same frequency spectrum. In such cases, the atrial sense amplifier threshold and band-pass are not useful for R-cross-wave rejection, and this signal is transmitted to the pacing logic as if it were a second natural P-wave.

Figure 4:
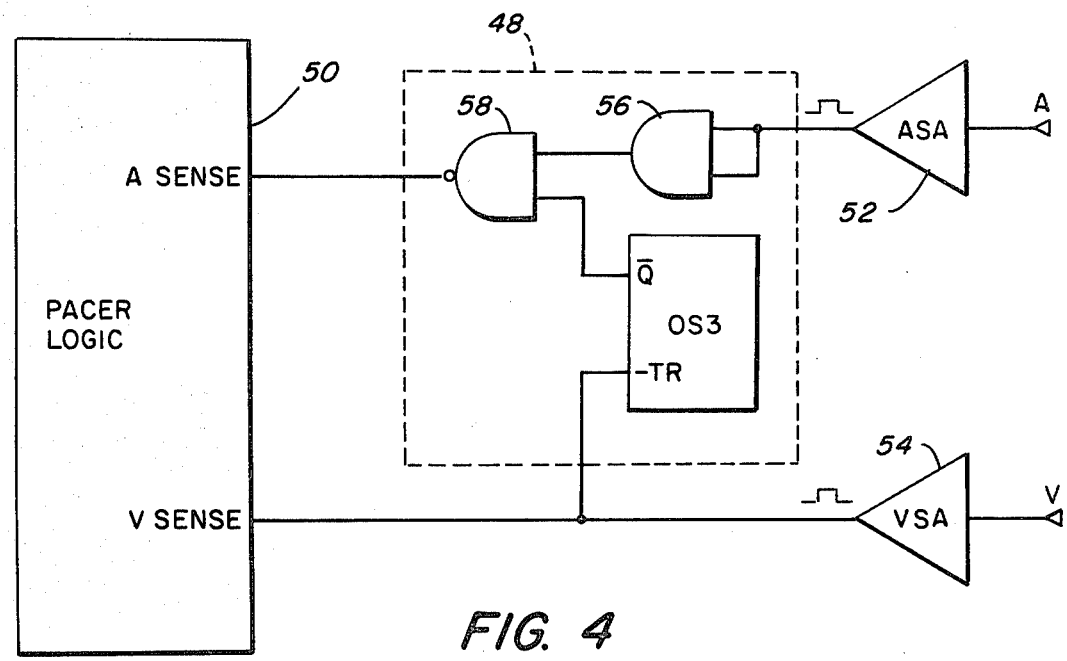
FIG. 4 and FIG. 5 are schematic diagrams of alternate logic circuits to prevent cross-sensing.

FIG. 4 illustrates a solution to this potential problem which can be achieved by modifying the circuitry inside the pacer 30 to incorporate cross-sense logic circuit 48 between the pacing logic 50 and both atrial and ventricular sense amplifiers 52 and 54. This circuit can be incorporated into the pacer 30 in any of the embodiments described herein. The binary output of the comparator output stage of ASA 52 is inverted in a first NAND gate 56 and fed to a second NAND gate 58. The other input to gate 58 is from a 50 ms one-shot OS3 which is triggered by the output of VSA 54, as shown in FIG. 4. An atrial signal occuring at the same time as an R-wave is rejected by the logic of the second NAND gate. The 50 ms delay provided by OS3 is necessary because of the delay occuring at the output of the two sense amplifiers (including, as usual, analog comparators at their outputs) as a consequence of the difference in amplitude and pulsewidth of the signals at their inputs.

By using logic circuit 48, or by introducing the equivalent logic in the software of a microprocessor-based pacer, the invention avoids cross-sensed pulses in the atria produced by normal or abnormal ventricular activity being sensed by the pacer logic as normal P-waves and producing incorrect pacer decisions. Retrograde conduction and premature ventricular contractions are particular cases of such abnormal ventricular activity.

Figure 5:
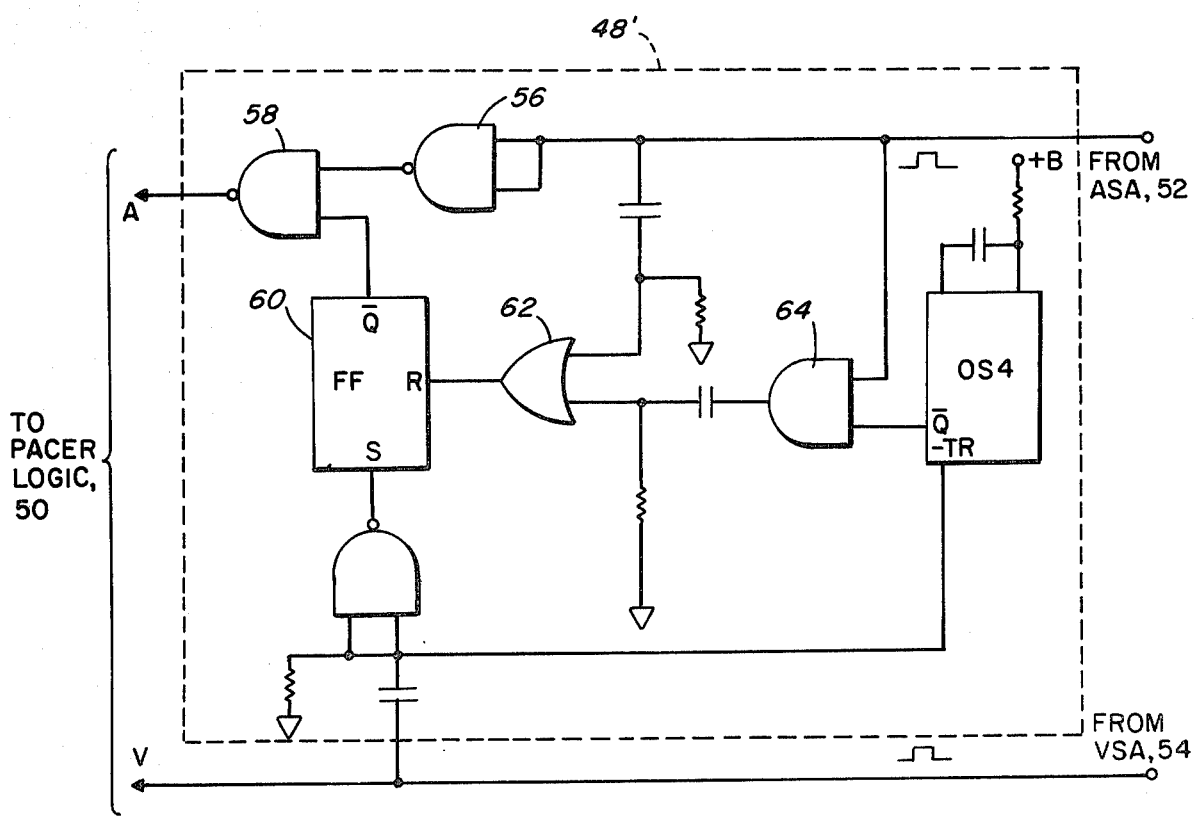

The logic circuit 48 shown in FIG. 4 (or FIG. 6) can be replaced by a slightly different one, circuit 48', illustrated in FIG. 5. In the embodiment of FIG. 5, the inhibition of the A signal is initiated by the appearance of the V signal and is removed by the end of the A signal (the positive going edge of the A signal). This strategy is implemented by the latch 60 which is set by a negative going V signal from VSA 54 and is reset via OR gate 62 by a positive going A signal. In the event that no cross-sensing is present while a V signal occurs (i.e., ASA output high), the timer OS4 resets latch 60 after a short delay (10-30 ms). Due to gate 64, the timer (OS4) has no effect if the output of the atrial sense amplifier is low (i.e., still sensing) when the astable period of one-shot OS4 expires.

Figure 6:
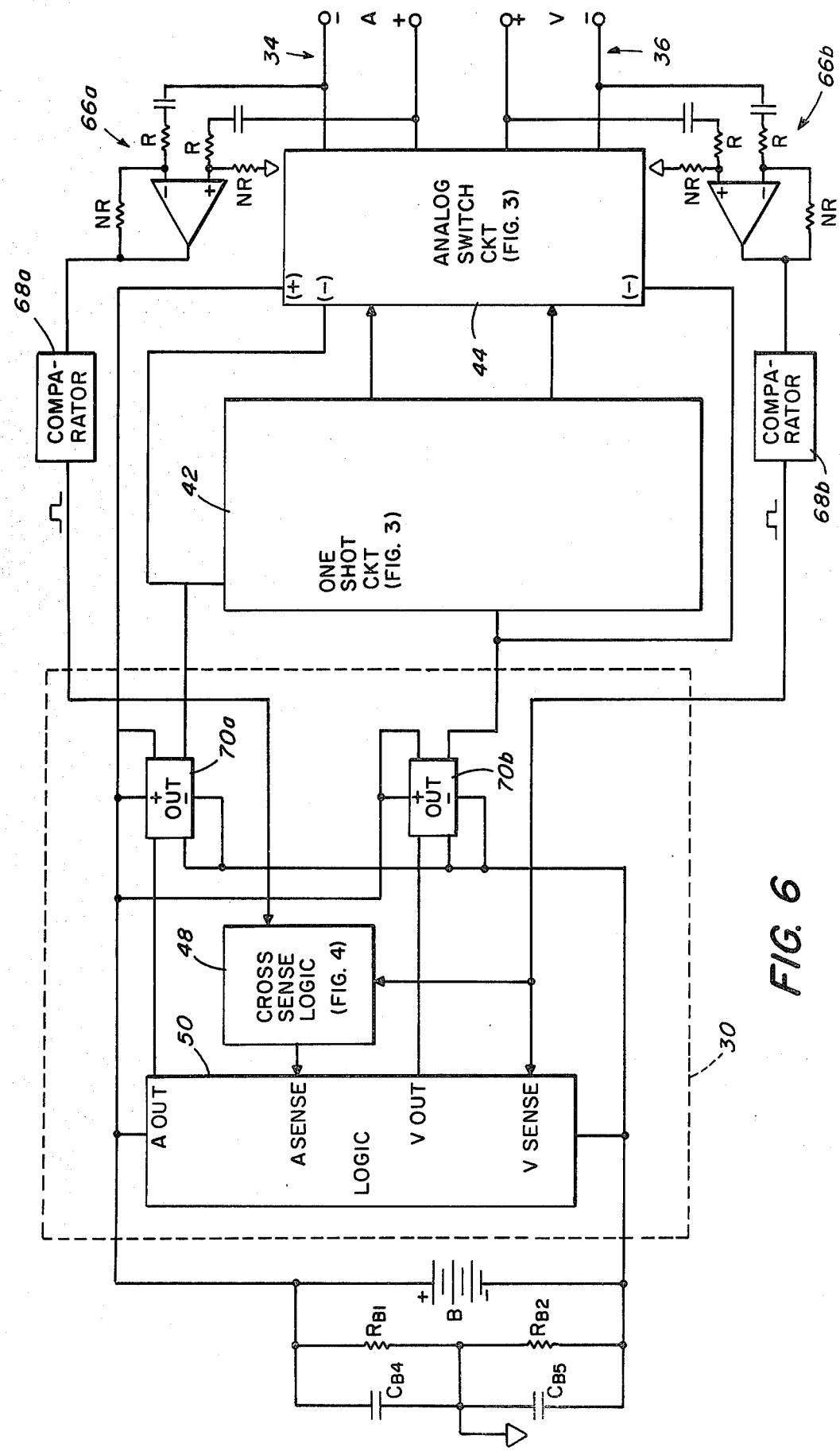
FIG. 6 is a schematic and block diagram of another embodiment of the interchannel isolation system according to the invention.

According to another embodiment of this invention, to minimize duplication, the pacer's sense amplifiers can be replaced by the two differential amplifiers used as buffers in FIG. 3. Differential amplifiers 66a and 66b in FIG. 6 can be provided with gain (e.g. N=400) and with the usual means for sensitivity adjustments. Their outputs are threshold detected as usual in comparators 68a and 68b. The amplifiers 66a and 66b presented in FIG. 6 are one-stage for the sake of simplicity; multi-stage amplifiers can be used. Anti-cross-sense logic circuit 48 (or 48') can be incorporated as shown in FIG. 6. The output circuits 70a and 70b form the output current pulses on command from pacer logic 50. The outputs of circuits 70a and 70b trigger one-shot circuit 42 and are passed to the leads via analog switch circuit 44 under the control of the one-shot circuit 42, as in FIG. 3.

Figure 7:
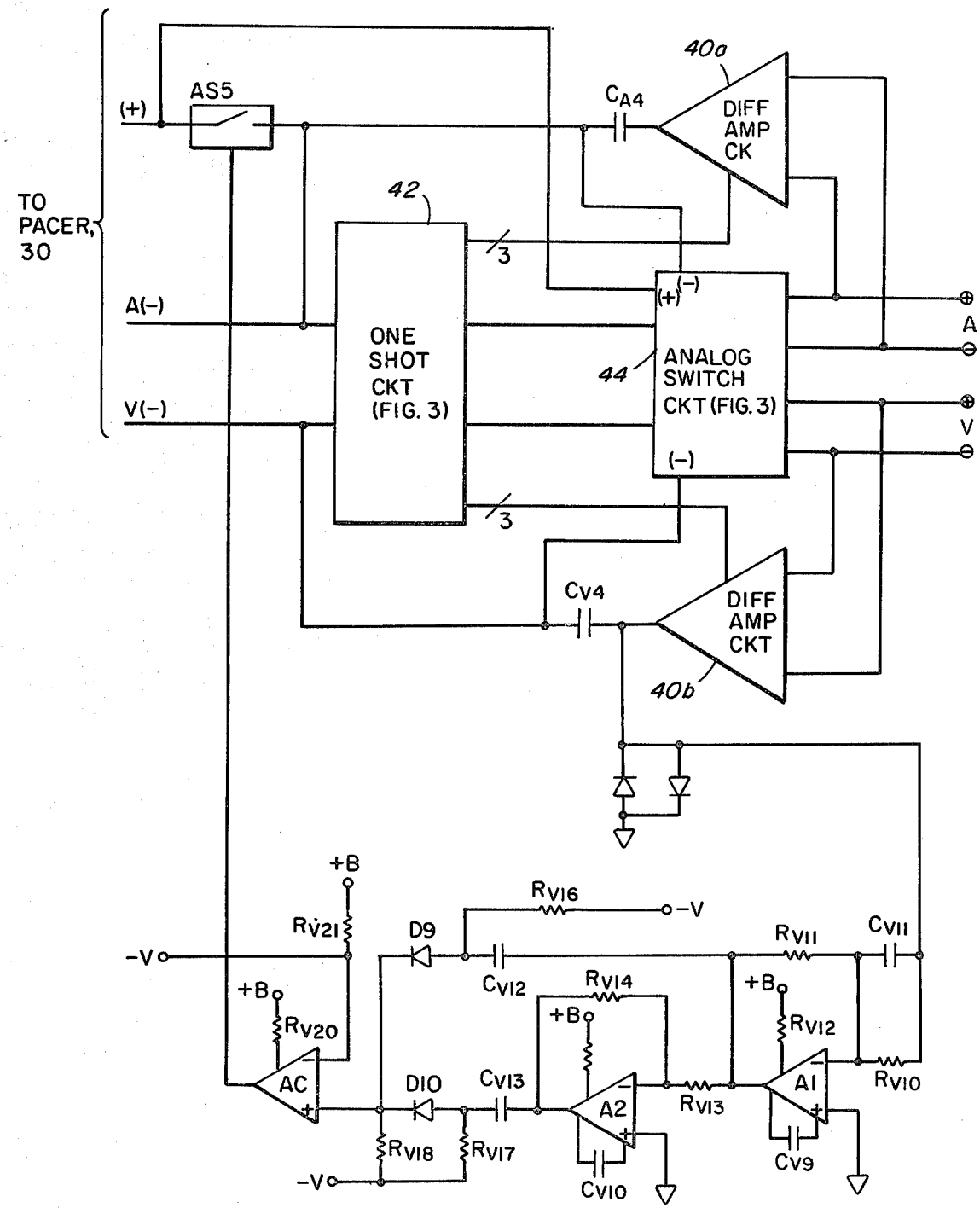
FIG. 7 is a block and schematic diagram of another embodiment of the interchannel isolation system provided with an anti-cross-sensing circuit.

In FIG. 7 the embodiment shown in FIG. 3 is provided with special circuitry for rejecting the naturally cross-sensed R-wave in the atrium. According to this embodiment of the invention, the derivative amplifier $A_1$ increases the level of the ventricular buffer differential amplifier output AD2, to the necessary level to trigger an analog comparator AC. An inverter A2 is provided to allow the comparator to be triggered by either positive or negative sensed signals. The output of the comparator AC controls the analog switch AS5. If a ventricular pulse (R-wave) is sensed, the atrial connection to the pacer's logic is interrupted by shunting the atrial terminal directly to positive reference potential.

The following table gives specific values of components suggested for the foregoing embodiments of the invention shown in FIGS. 2-7. These component values are only illustrative and are not intended in any way to define or limit the selection of components or values for these or other circuits within the scope of the invention.

TABLE

| | |
|---|---|
| $R_{V1} = R_{A1}$ | 25 kilohms |
| $R_{V2} = R_{A2}$ | 51 kilohms |
| $R_{V3} = R_{A3}$ | 100 kilohms |
| $R_{V4} = R_{A4}$ | 1 megohm |
| $R_{V5} = R_{A5}$ | 25 megohms |
| $R_{V6} = R_{A6}$ | megohms |
| $R_{V7} = R_{A7}$ | megohms |
| $R_{V8} = R_{A8}$ | megohms |
| $R_{V9} = R_{A9}$ | 10 megohms |
| $R_{V10}$ | 10 kilohms |
| $R_{V11}$ | 5.6 megohms |
| $R_{V12}$ | 20 megohms |
| $R_{V13}$ | 1 megohm |
| $R_{V14}$ | 1 megohm |
| $R_{V15}$ | 20 megohms |
| $R_{V16}$ | 0.2 megohm |
| $R_{V17}$ | 0.2 megohm |
| $R_{V18}$ | 5 megohms |
| $R_{V19}$ | 0.7 megohm |
| $R_{V20}$ | 40 megohms |
| $R_{V21}$ | 10 megohms |
| $R_{B1} = R_{B2}$ | 5 megohms |
| $R_{B3}$ | 50 megohms |
| $C_{V1} = C_{A1}$ | 0.1 microfarad |
| $C_{V2} = C_{A2}$ | 0.1 microfarad |
| $C_{V3} = C_{A3}$ | 0.1 microfarad |
| $C_{V4} = C_{A4}$ | 1 microfarad |
| $C_{V5} = C_{A5}$ | 0.1 microfarad |
| $C_{V6} = C_{A6}$ | 2.5 microfarads |
| $C_{V7} = C_{A7}$ | 2.5 microfarads |
| $C_{V8} = C_{A8}$ | 220 picofarads |
| $C_{V9}$ | 220 picofarads |
| $C_{V10}$ | 220 picofarads |
| $C_{V11}$ | 1 microfarad |
| $C_{V12}$ | 3.3 microfarads |
| $C_{V13}$ | 3.3 microfarads |
| $C_{B1} = C_{B2}$ | 2.2 microfarads |
| $C_{B3}$ | 100 microfarads |
| $C_{B4} = C_{B5}$ | 0.1 microfarad |

The foregoing circuits offer the advantage of retrofitting existing pacer circuitry to reduce crosstalk by using the stimulation pulse itself to trigger direct connection of the corresponding leads to the pacer while avoid common ground. Unlike conventional bipolar pacers, at no time are the anodes of the leads connected directly to the same positive reference potential. Thus, the well known advantages of bipolar leads can be obtained with existing pacing circuitry without the formerly attendant disadvantage of increased interchannel interference. Any of the foregoing timing or logic functions can of course be implemented by discrete digital or microprocessor applications.

By using simple logic circuits (or by introducing equivalent logic in the software of a microprocessor-based pacer), the invention avoids cross-sensed pulses in the atria produced by normal or abnormal ventricular activity, being sensed by the pacer logic as normal P-waves and producing incorrect pacer decisions, retrograde conduction and premature ventricular contractions being particular cases of such abnormal ventricular activity.

Variations and adaptations the above-described circuitry consistent with the fundamental principles may be made without departing from the spirit and scope of the invention as defined by the appended claims and equivalents thereto.

What is claimed is:

1. A cardiac pacer of the type comprising a stimulation pulse generator having a common terminal, first and second input/output terminals and two bipolar leads each having first and second distal electrodes, corresponding ones of which are coupled to said common terminal and the respective input/output terminals, wherein the improvement comprises:

means between each of said bipolar leads and the pulse generator for electrically isolating said leads from each other, and means responsive to an output stimulation pulse from the pulse generator for temporarily connecting the corresponding lead directly to the common terminal and the corresponding input/output terminal bypassing said isolation means for an interval covering the stimulation pulse width, said isolation means including two resistances in series respectively with the electrodes coupled to said common terminal, and two buffer amplifier means in series respectively with the other electrodes of said leads for supplying the respective input/output terminal with a buffered amplified signal representing the signal picked up on the respective lead.

2. A cardiac pacer of the type comprising a stimulation pulse generator having a common terminal, first and second input/output terminals and two bipolar leads each having first and second distal electrodes, corresponding ones of which are coupled to said common terminal and the respective input/output terminals, wherein the improvement comprises:

means between each of said bipolar leads and the pulse generator for electrically isolating said leads from each other, and means responsive to an output stimulation pulse from the pulse generator for temporarily connecting the corresponding lead directly to the common terminal and the corresponding input/output terminal bypassing said isolation means for an interval covering the stimulation pulse width, said connecting means including at least one one-shot means responsive to a stimulation output pulse from said pulse generator for producing a control signal lasting at least as long as said stimulation pulse, and switch means in parallel with said isolation means responsive to said control signal for connecting the corresponding lead directly to said pulse generator for feeding said stimulation pulse substantially undiminished to the heart.

3. The pacer of claim 2, wherein said connecting means includes two one-shot means responsive respectively to stimulation output pulses from the input/output terminals of the pulse generator for producing corresponding control signals each lasting at least as long as said stimulation pulse, and two switch means in parallel respectively with said isolation means responsive to the corresponding control signal for connecting the corresponding lead directly to the respective terminals of said pulse generator to feed the stimulation pulse substantially undiminished to the heart.

4. The pacer of claim 3, wherein said connecting means further includes voltage doubler means operatively connected between each said one-shot means and switch means, responsive to said control signal, for applying increased voltage to said switch means compatible with an increased voltage output stimulation pulse.

5. The pacer of claim 2, wherein said isolation means includes two differential amplifiers each having its complementary inputs coupled to the electrodes of the corresponding lead and its output connected to the respective input/output terminal of said pulse generator.

6. The pacer of claim 5, wherein said connecting means includes two one-shot means responsive respectively to stimulation output pulses from the input/output terminals of the pulse generator for producing corresponding control signals each lasting at least as long as said stimulation pulse, and two pairs of switch means in parallel respectively with each electrode of each lead and the output of the corresponding differential amplifier, responsive to the respective control signal, for connecting the corresponding lead directly to the respective terminals of said pulse generator bypassing said differential amplifier to feed the stimulation pulse substantially undiminished to the heart.

7. The pacer of claim 6, wherein said connecting means further includes voltage doubler means operatively connected between said one-shot means and switch means responsive to the corresponding control signals for applying increased voltage to said switch means compatible with an increased voltage output stimulation pulse.

8. The pacer of claim 5, wherein the improvement further comprises power supply means forming a common ground between positive and negative terminals of said battery, said differential amplifying means being operatively connected to said common ground.

9. The pacer of claim 8, wherein said power supply means further includes filtering means connected across said battery to alleviate voltage transients due to stimulation pulses.

10. A dual chamber bipolar lead cardiac pacer, comprising atrial and ventricular leads each having a pair of distal electrodes, and an implantable electronic module including a power supply having a battery and means defining a common ground between the positive and negative terminals of said battery, atrial and ventricular differential amplifying means with substantial gain operatively connected to said power supply having their inputs connected to the respective pairs of lead electrodes, pacing logic means powered by said battery having atrial and ventricular sense and output command terminals for processing sensed signals and issuing appropriate output commands for cardiac pacing, atrial and ventricular comparator means for threshold-detecting the magnitude of the outputs of the respective amplifying means to produce digital outputs to the respective sense terminals, cross-sensing logic means for gating the comparator output to the atrial sense terminal as a function of the ventricular comparator output, atrial and ventricular output circuits responsive to a corresponding output command from said pacing logic means for producing a corresponding electrical output, and first and second switch means responsive to the electrical output from the corresponding output circuit for connecting the corresponding lead electrodes to one side of said battery and to the output of the corresponding output circuit, respectively, for a predetermined interval.

11. The pacer of claim 10, wherein said cross-sensing logic means includes one-shot means responsive to a ventricular comparator output for nullifying the effects of the atrial comparator output for a predetermined interval.

* * * * *